United States Patent [19]

Lane et al.

[11] Patent Number: 4,654,436

[45] Date of Patent: Mar. 31, 1987

[54] CARBONYLATION PROCESS FOR THE PRODUCTION OF AROMATIC ACIDS OR ESTERS

[75] Inventors: Donald W. Lane; Thomas H. Larkins, Jr.; Mark Rule, all of Kingsport, Tenn.

[73] Assignee: Eastman Kodak Company, Rochester, N.Y.

[21] Appl. No.: 887,488

[22] Filed: Jul. 21, 1986

Related U.S. Application Data

[63] Continuation-in-part of Ser. No. 772,784, Sep. 5, 1985, abandoned.

[51] Int. Cl.$^4$ .............................................. C07C 67/36
[52] U.S. Cl. ...................................... 560/80; 560/97; 560/100; 560/103; 562/406
[58] Field of Search ................... 560/80, 97, 100, 103; 562/406

[56] References Cited

U.S. PATENT DOCUMENTS

| | | | |
|---|---|---|---|
| 2,565,463 | 8/1951 | Tabet | 562/406 |
| 2,914,554 | 11/1959 | Kroeper | 560/103 |
| 3,733,354 | 5/1973 | Cassar | 562/406 |
| 3,988,358 | 10/1976 | Heck | 560/97 |
| 3,996,288 | 12/1976 | Yukata | 562/406 |

FOREIGN PATENT DOCUMENTS 81835  7/1959  United Kingdom .

Primary Examiner—Michael L. Shippen
Attorney, Agent, or Firm—Charles R. Martin; J. Frederick Thomsen

[57] ABSTRACT

This invention relates to a novel carbonylation process for the production of aromatic carboxylic acids or esters of aromatic. More particularly, this invention relates to a process for the carbonylation of aromatic iodides or bromides with carbon monoxide in the presence of a palladium catalyst promoted with a Group VIB carbonyl and in the presence of an alcohol or water in a base reaction medium having a pKa greater than about 8. When the alcohol is used the product is the ester. When water is used the product is the carboxylic acid.

11 Claims, No Drawings

CARBONYLATION PROCESS FOR THE PRODUCTION OF AROMATIC ACIDS OR ESTERS

This is a continuation in part of U.S. application Ser. No. 772,784 filed Sept. 5, 1985, now abandoned.

This invention relates to a novel carbonylation process for the production of aromatic carboxylic acids or esters. More particularly, this invention relates to a process for the carbonylation of aromatic iodides or bromides with carbon monoxide in the presence of a palladium catalyst promoted with a group VIB carbonyl in a base reaction medium having a pKa greater than about 8.

The preparation of carboxylic acid derivatives by carbonylation of aromatic halides catalyzed by Group VIII metal compounds is well known in the art. One such process is described in U.S. Pat. No. 2,640,071 whereby carboxylic acid derivatives are obtained from aromatic halides in a strong base reaction medium using nickel complexes as catalyst at high reaction temperatures of 250°–450° C. and a carbon monoxide pressure of 300 to 1,000 atmospheres. A typical example is the conversion of p-dichlorobenzene to dialkyl terephthalate at 345° C. and 350 atmospheres of carbon monoxide in the presence of a catalytic amount of nickel. This process requires both high temperatures and pressure.

Another carbonylation process for preparing carboxylic acid derivatives known in the art is described in U.S. Pat. No. 3,988,358 whereby aromatic carboxylic acid esters are prepared from aromatic halides by the reaction of a starting material such as bromobenzene in a basic reaction medium with an alcohol, such as butanol, and carbon monoxide in the presence of a palladium catalyst complexed with a ligand such as a tertiary amine or phosphines, for example. However, the reaction rates obtained with aryl bromides are unacceptably slow from a commercial standpoint.

Such processes are undesirable due to the high energy needed for the high reaction temperatures, complex catalyst systems and moderate product yields.

It would therefore be an advance in the state of the art to provide an improved process for carbonylation of aromatic iodides or bromides to prepare aromatic carboxylic acids or esters with improved rates.

In accordance with the present invention, it has been found that aromatic iodides or bromides can be carbonylated to the desired aromatic carboxylic acids or esters of aromatic carboxylic acids with improved rates by reaction with carbon monoxide in the presence of a palladium catalyst promoted with a group VIB carbonyl in a base reaction medium having a pKa greater than about 8. Furthermore, the reaction has high selectivity in the formation of the aromatic carboxylic acid or ester in high purity with little or no formation of products such as aromatic carboxyl aldehydes such as 4-carboxybenzaldehyde.

The aromatic iodide or bromide employed as a starting material in the process of the present invention has the formula:

wherein R represents a carbocyclic or heterocyclic aromatic group having about 5 to about 20 atoms in the ring or rings thereof and n is an integer of from 1 to about 4 and X is a bromine or iodine. Such R groups can be, for example, benzene, naphthalene, pyridine, thiophene, pyrrole, and the like. The R groups can be substituted or unsubstituted. Such substituted R groups include as substituents halides such as chlorine and bromine, alkyl groups having up to about 12 carbon atoms, vinyl groups, carboxylic acid groups, ester groups, ether groups, and the like. Such compounds are, for example, iodobenzene, 1,3-diiodobenzene, 1,4-diiodobenzene, 2,6-diiodonaphthalene, 2,7-diiodonaphthalene, bromobenzene, 1,4-dibromobenzene, and the like.

The aromatic iodides or bromides employed in the process of the present invention are known in the art and can be prepared by the methods known in the art. For example, T. Hudlicky et al in *The Chemistry of Halides, Pseudohalides and Azides,* Supplement D, Part 2, 1142–1158, the disclosure of which is incorporated herein by reference discloses some of such processes. One such specific process is described in J. Chem. Soc. 150 (1952) which discloses preparing iodoaromatic compounds by treatment of the aromatic compound such as benzene with iodine in the presence of silver sulfate dissolved in concentrated sulfuric acid.

The palladium catalyst is added to the reaction medium preferably as the zero-valent form of the metal such as palladium black, palladium sponge and palladium shot, and the like. More preferably, the zero-valent metal is supported on a suitable material. Such supports may be for example, carbon, alumina, silica, kieselguhr, barium carbonate, barium sulfate, calcium carbonate and the like. The amount of palladium on such support can be any desirable amount such as, for example, about 1 to 10 percent by weight. For example, a highly desirable catalyst material comprises 5% palladium on a carbon support. Of course, other zero-valent catalyst forms can be employed.

The catalyst metal may also be provided in a higher valence state, provided that an in situ reduction to the zero-valent form occurs. Thus, palladium salts, such as palladium acetate, palladium chloride, tetrakis(triphenylphosphine)palladium, tetraaminepalladium nitrate, potassium tetrachloropallodate, palladium acetylacetonate, palladium oxide, dichloro-bis(acetonitrile)palladium, dichloro(1,5-cyclooctadiene)palladium, lithium tetrachloropalladate, allylpalladium chloride dimer, ammonium hexachloropalladium, bis(acetonitrile)-dichloropalladium, diamine-dichloropalladium, trans-dichlorobis(benzonitrile)palladium, palladium cyanide, palladium nitrate, potassium hexachloropalladium, and the like, are also suitable catalyst materials. The amount of palladium present is about 0.05 to 5 mole percent, preferably, about 0.1 to 1 mole percent, based on the aromatic bromide or iodide.

The promoters or rate enhancers added to the palladium catalyst are group VIB cabonyls. Such carbonyls are, for example, chromium hexacarbonyl, molybdenum hexacarbonyl and tungsten hexacarbonyl. The carbonyl promoter can be added to the reaction mixture or formed in situ. The chromium carbonyl gives greater catalyst enhancement than either molybdenum or tungsten. The amount of group VIB carbonyl added is from about 0.05 weight percent to 10 weight percent based on the weight of palladium used as the catalyst.

The reaction is carried out in a base reaction medium having a pKa of at least 8, preferably about 8.0 to about 11.0. The presence of such a base prevents the deactivation of the catalyst. The base used can be an organic base or an inorganic base. The base is present in an amount of about 1 mole base to 1 mole aryl halide to about 10 mole base to 1 mole aryl halide, preferably 1 mole aryl halide to 3 mole base, which provides a reaction medium having a pKa of at least 8. Bases which have been particularly useful are, for example, sodium hydroxide, sodium carbonate, sodium acetate, trialkyl amines such as trimethylamine, triethylamine, tributylamine, and the like.

Inert coordinating solvents may be employed, but are not necessary. Such solvents include, for example, tetrahydrofuran, acetonitrile, and the like. In preparing aromatic esters by the reaction of an aromatic iodide or bromide with carbon monoxide and an alcohol, the alcohol can be employed as solvent.

The catalytic carbonylation reaction of the present invention is conducted in the presence of carbon monoxide, which is employed in amounts such that the total reaction pressure is in the range of 0 psig to about 1500 psig (about 7 kPa to about 10,500 kPa). Pressures greater than atmospheric pressure may be employed when a volatile reactant or reaction medium is employed. However, the metal carbonyl promoter is less effective at higher carbon monoxide pressures. Therefore, reaction pressures from about 0 psig. to about 100 psig (about 7 kPa to about 700 kPa) are preferred.

The process of the present invention can be conducted at temperatures of about 50° C. to about 180° C., preferably about 80° C. to 150° C., most preferred 100° C. to 125° C. At temperatures less than 50° C. the reaction rate is slow and above 180° C., there is a reduction in product yield and above 250° C. product decomposition occurs.

The aromatic halide is added to the reaction medium in an amount of about 0.1 to 50 weight percent, based on the total weight of the reaction medium. An amount less than 0.1 provides a reaction rate too slow to be economically feasible and an amount greater than 50 percent adversely affects the solubility of the reactant in the reaction medium.

Since substantially no intermediates such as aldehydes are formed during the carbonylation, the process of the present invention provides aromatic acids or esters of very high purity. Such polycarboxylic acids, as for example, the terephthalic acid and naphthalene dicarboxylic acid are suitable for preparing polyesters without further purification as by the preparation of the diesters. This is a significant advance in the state of the art since other processes for preparing such acids as by the oxidation of xylene and 2,6-dimethyl naphthalene provide significant amounts of impurities such as the aldehydes which require removal prior to use of the polycarboxylic acids in polyester processes.

There are two embodiments to this invention. One embodiment involves conducting the process of the invention in the presence of an alcohol. When this embodiment is practiced the result is production of an ester of an aromatic carboxylic acid. The alcohols useful in this embodiment correspond to the formula

R—OH where R can be an aliphatic residue containing from 1 to 20 carbon atoms, an alicyclic residue containing from 4 to 6 carbon atoms or an aromatic residue containing 10 carbon atoms. Broadly, between 1 mole and 10 moles of the alcohol can be used per mole of aromatic halide. Preferably about 5 moles of alcohol per mole of aromatic halide are used.

The other embodiment of the invention involves conducting the process in the presence of water. When this embodiment is practiced the result is production of an aromatic carboxylic acid. Broadly between 1 and 10 moles of water can be used per mole of aromatic halide. Preferably about 5 moles of water per mole of aromatic halide are used.

Combinations of alcohol and water can be used to produce a product which is partly an aromatic dicarboxylic acid and partly an ester of the aromatic carboxylic acid. The combined amount of alcohol and water is within the same molar range as when only alcohol or only water is used.

The novel process of the present invention therefore provides a process which provides improved rates of high purity products which are useful intermediates in the synthesis of polyesters such as polyethylene terephthalate, and other useful polymeric products.

The invention will be further illustrated by the following Examples although it will be understood that these Examples are included merely for purposes of illustration and are not intended to limit the scope of the invention.

EXAMPLE 1

Into a 300 cc autoclave was added 10 grams bromobenzene, 0.5 gram of 5% palladium on carbon, 100 grams n-butanol, 12 grams tributyl amine and 0.7 grams chromium hexacarbonyl. Carbon monoxide was fed beneath the surface of the refluxing mixture at a pressure of 25 psi and the reaction mixture was heated at 125° C. for two hours. About 7.5 grams of butyl benzoate was recovered. The conversion to butyl benzoate based on the amount of bromobenzene employed was 67 percent.

EXAMPLE 2

Example 1 is repeated except that the chromium carbonyl is deleted. The conversion to butyl benzoate based on the amount of bromobenzene is only 16 percent.

EXAMPLE 3

Example 1 is repeated except that 15 grams of dibromobenzene is used in place of the 10 grams bromobenzene. The recovered product was 17.5 grams which on analysis contained 73 percent dibutyl terephthalate and 25 percent butyl bromobenzoate. The yield of dibutyl terephthalate based on the dibromobenzene is 73 percent.

EXAMPLE 4

Example 1 is repeated except that 15 grams of iodobenzene is used in place of the 10 grams bromobenzene and 100 grams of water was used as the solvent in place of 100 grams n-butanol. The recovered solid product was 8.5 grams which was analyzed as 100% benzoic acid. The yield of benzoic acid based on iodobenzene is 94.7 percent.

EXAMPLE 5

Example 1 is repeated except that molybdenum hexacarbonyl is used in place of the chromium hexacarbonyl. The recovered product was 7.4 grams with a yield of butyl benzoate based on bromobenzene of 58 percent.

EXAMPLE 6

Example 5 is repeated except that 0.7 grams tungsten hexacarbonyl is used in place of the 0.7 grams molybdenum hexacarbonyl. The recovered benzoate product was 7.6 grams or a yield of butyl benzoate based on the bromobenzene of 48 percent.

EXAMPLE 7

Into a 330 cc autoclave was added 10 grams bromobenzene, 0.5 gram 5% palladium on carbon, 100 grams n-butanol, 12 grams tributyl amine and 0.7 gram chromium hexacarbonyl. Carbon monoxide was fed beneath the surface of the reaction mixture at a pressure of 250 psi and the reaction mixture was heated at 125° C. for two hours. The benzoate product recovered was 3.1 grams. The conversion to benzoate based on the amount of bromobenzene employed was only 27 percent.

The carboxylic acids and esters prepared by the present invention are well known in the art and are useful for many purposes. For example, the polycarboxylic acids can be used in preparing thermoplastic compositions such as polyesters. Such polyesters can be formed into film, fibers, coatings and molded objects.

EXAMPLE 8

Into a 330 cc autoclave was added 10 grams bromobenzene, 0.5 gram 5% palladium on carbon, 100 grams of methanol, 12 grams of tributylamine and 0.7 gram of chromium hexacarbonyl. Carbon monoxide was fed beneath the surface of the reaction mixture at a pressure of 100 psig and the reaction mixture heated at 125° C. for two hours. The methyl benzoate recovered was 7.2 grams, representing a conversion of 83%. When the reaction was repeated with the omission of the chromium hexacarbonyl, the amount of methyl benzoate was 1.7 grams, representing or conversion of 20%.

The invention has been described in detail with particular reference to preferred embodiments thereof, but it will be understood that variations and modification can be effected within the spirit and scope of the invention.

We claim:

1. A process for the preparation of aromatic carboxylic acid esters which comprises reacting an aromatic halide having the formula $$R(X)_n$$

wherein R is a substituted or unsubstituted aromatic ring having about 5 to about 14 atoms in the ring or rings thereof, X is bromine or iodine and n is an integer of 1 to about 4 with carbon monoxide in the presence of a palladium catalyst promoted with a group VIB carbonyl and in the presence of an alcohol corresponding to the formula $$R\text{---}OH$$

where R can be an aliphatic residue containing from 1 to 20 carbon atoms, an alicyclic residue containing from 4 to 6 carbon atoms or an aromatic residue containing 6 to 10 carbon atoms in a base reaction medium having a pKa greater than about 8.

2. A process according to claim 1 wherein said R is a phenyl group.

3. A process according to claim 1 wherein said R is a naphthyl group.

4. A process according to claim 2 wherein said X is bromine and said n is 2.

5. A process according to claim 3 wherein said X is bromine and said n is 2.

6. A process according to claim 3 wherein said X is iodine and said n is 2.

7. A process according to claim 3 wherein said X is iodine and said n is 2.

8. A process according to claim 4 wherein said Group VIB carbonyl is chromium hexacarbonyl.

9. A process according to claim 4 wherein said group VIB carbonyl is molybdenum hexacarbonyl.

10. A process according to claim 4 wherein said group VIB carbonyl is tungsten hexacarbonyl.

11. A process for the preparation of esters of aromatic carboxylic acids which comprises reacting an aromatic halide having the formula $$R(X)_n$$

wherein R is a substituted or unsubstituted aromatic ring having about 5 to about 14 atoms in the ring or rings thereof, X is bromine or iodine and n is an integer of 1 to about 4 with carbon monoxide in the presence of a palladium catalyst promoted with a group VIB carbonyl and in the presence of water in a base reaction medium having a pKa greater than about 8.

* * * * *